United States Patent [19]

Norman et al.

[11] Patent Number: 4,898,169

[45] Date of Patent: Feb. 6, 1990

[54] MEDICAL INSTRUMENT FOR THERAPY OF HEMORRHOIDAL LESIONS

[75] Inventors: Daniel A. Norman; Ronald R. Newton, both of Stateline, Nev.; Glenn V. Nicholas, Walnut Creek, Calif.; Steven Bellofatto, Closter, N.J.; Stephen K. Onody, Sherborn, Mass.

[73] Assignee: Boston Scientific Corporation, Watertown, Mass.

[21] Appl. No.: 213,597

[22] Filed: Jun. 30, 1988

Related U.S. Application Data

[63] Continuation-in-part of Ser. No. 47,698, May 8, 1987, abandoned, and a continuation-in-part of Ser. No. 47,712, May 8, 1987, and a continuation-in-part of Ser. No. 48,374, May 11, 1987, abandoned.

[51] Int. Cl.$^4$ .............................................. A61B 17/36
[52] U.S. Cl. .................................. 606/42; 128/419 R
[58] Field of Search ........... 128/303.1, 303.13, 303.14, 128/303.15, 303.17, 419 R, 421

[56] References Cited

U.S. PATENT DOCUMENTS

| | | | |
|---|---|---|---|
| 703,369 | 7/1902 | Batcheller | 128/303.17 |
| 2,327,874 | 8/1943 | De Jong | 128/800 |
| 2,447,127 | 8/1948 | Landauer | 128/800 |
| 3,132,645 | 5/1964 | Gasper | 128/3 |
| 3,985,137 | 10/1976 | Donohue | 128/303.17 |
| 4,016,881 | 4/1977 | Rioux et al. | 128/303.17 |
| 4,074,110 | 2/1978 | Slaughter | 128/303.1 |
| 4,090,517 | 5/1978 | Nagatoki | 128/303.1 |
| 4,196,734 | 4/1980 | Harris | 128/303.1 |
| 4,266,547 | 5/1981 | Komiya | 128/303.1 |
| 4,498,475 | 2/1985 | Schneiderman | 128/303.13 |
| 4,520,825 | 6/1985 | Thompson et al. | 128/419 PG |
| 4,598,713 | 7/1986 | Hansjürgens et al. | 128/419 PG |
| 4,621,635 | 11/1986 | Ali | 128/303.1 |
| 4,638,806 | 1/1987 | Bartlett | 128/400 |
| 4,711,239 | 12/1987 | Sorochenko et al. | 128/303.14 |

OTHER PUBLICATIONS

The Endo-Lase Literature.
Norman et al. Abstract and Draft Article.
Products—Exhibit A.
U.S. Ser. No. 048,374.
Templeton et al., "Comparison of Infrared Coagulation and Rubber Band Ligation for First and Second Degree Haemorrhoids: A Randomised Prospective Clinical Trial", British Medial Journal, vol. 286, Apr. 30, 1983, pp. 1387–1389.
Ambrose et al., "Prospective Randomised Comparison of Photocoagulation and Rubber Band Ligation in Treatment of Haemorrhoids", British Medical Journal, vol. 286, Apr. 30, 1983, p. 1389.
Excerpt from Proctosigmoidoscopy.
Wilbur E. Keesey, M.D., "Obliteration of Hemorrhoids with Negative Galvanism", *Official Journal American Congress of Physical Therapy*, Sep. 1934.
J. Curtis Webb, "The Treatment of Haemorrhoids by Electrolysis", *British Medical Journal*, Mar. 26, 1921.
The ACMI Literature.

*Primary Examiner*—Francis Jaworski
*Assistant Examiner*—George Manuel
*Attorney, Agent, or Firm*—Fish & Richardson

[57] ABSTRACT

An instrument for direct current electrical therapy of hemorrhoidal lesions or the like in a patient consists of a D.C. electric generator, a grounding pad, a probe with distal tip for penetration of a lesion, and a handpiece for support of the probe and control of the level of current. The probe has a base and at least one electrode terminating in the distal tip. The handpiece has a lower handle to be gripped by a physician. The probe base is coupled to the handpiece, with the probe axis at an obtuse angle to the lower handle axis, the angle selected to allow a physician to hold the instrument without extended abnormal wrist flexure. Disposed generally above the lower handle is a front panel visible to the physician when the probe tip is penetrated into a lesion. The front panel includes a display of conditions disposed generally the line of sight of a physician with the probe tip. Controls for the level of current are disposed to allow a physician to operate the controls with digits of a hand gripping the handle.

14 Claims, 14 Drawing Sheets

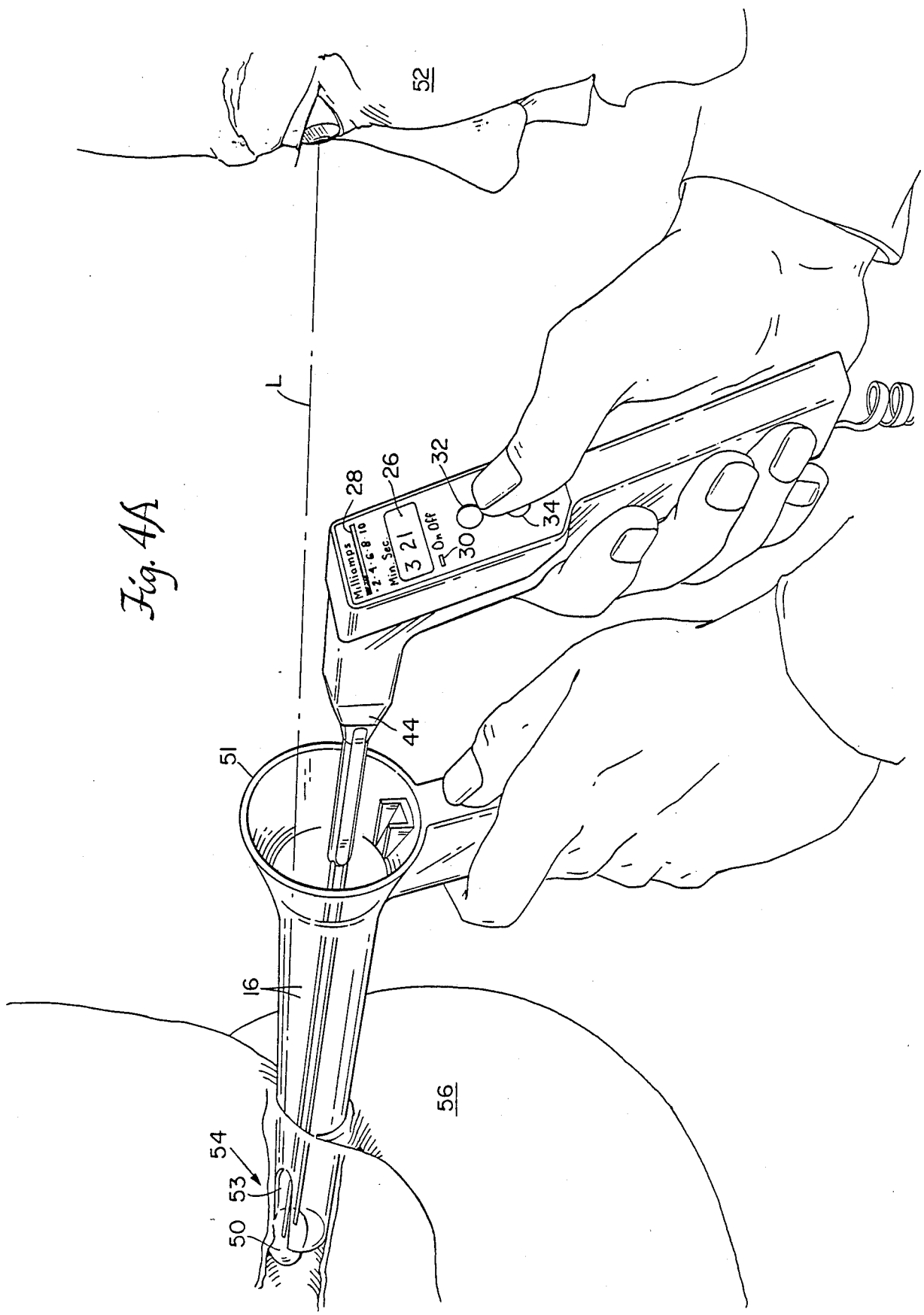

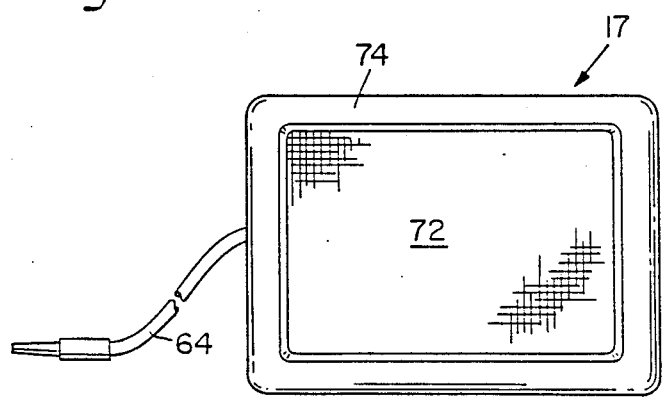
Fig. 6
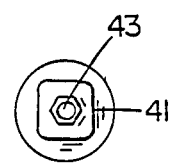
Fig. 5A
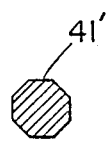
Fig. 5C
Fig. 7
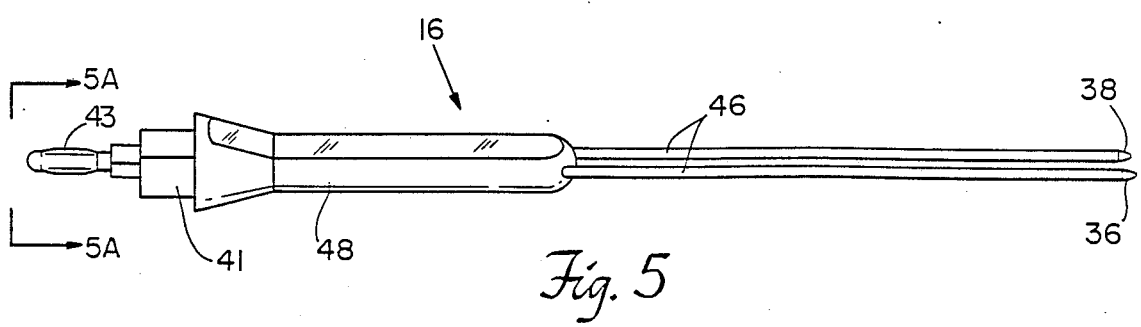
Fig. 5
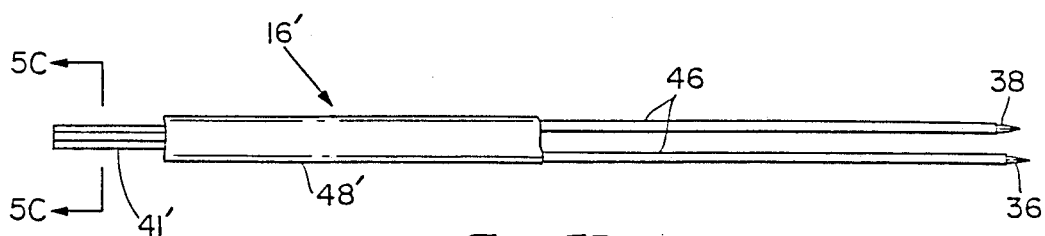
Fig. 5B

ADJUST WITH MILLIAMP
METER TO 20 MA MAX. SCALE

MEDICAL INSTRUMENT FOR THERAPY OF HEMORRHOIDAL LESIONS

This application is a continuation-in-part of U.S. Ser. No. 047,698 now abandoned and U.S. Ser. No. 047,712, both filed May 8, 1987 and of U.S. Ser. No. 048,374, filed May 11, 1987 now abandoned.

The invention relates to an electrical current therapy device for treatment of hemorrhoids or the like.

Hemorrhoidal disease is one of the most frequent, disabling, and painful conditions of mankind. The consensus of the Advisory Panel of the U.S. Food and Drug Administration defines hemorrhoids as "abnormally large or symptomatic conglomerates of blood vessels, supporting tissues, and overlying mucous membrane or skin of the anorectal area."

It is estimated that one-third of the U.S. population has symptomatic internal hemorrhoids, with an incidence of 50% at age 50 years. Patients frequently postpone examination because of concern of pain associated with a particular treatment modality, hospitalization, cost, and time of disability. Such a delay in evaluation may lead to progression of the hemorrhoidal disease, or late diagnosis of more serious colorectal problems.

Medical procedures for hemorrhoidal treatment have taken many forms. For example, D.C. (direct current) management of hemorrhoidal disease was described in a review published by Wilbur E. Keesey, M.D. in 1934. The topical suppository approach is presently applied to a majority of patients, particularly those with a specific precipitating factor for hemorrhoidal disease (e.g., acute diarrhea episode) and in some instances may be all that is necessary. Necrosis and slough of hemorrhoidal vessels can also, at times, be accomplished by placement of rubber bands over the vessel base with a specific apparatus. This treatment is applicable to those vessels well above the pectinate line to avoid severe pain (a complication in 6 to 10% of patients). Mild to moderately diseased hemorrhoidal vessels are not amenable to this therapy. Injection sclerotherapy is effective for small (grade 1 and 2) bleeding internal hemorrhoids. Submucosal injection of sclerosant produces chemical thrombosis and fixation of the mucosa to the underlying tissue. Sclerotherapy of hemorrhoids is limited to mild to moderate disease and is associated with complications including reaction to the injected material, slough of the overlying mucosa, necrosis, and infection, including submucosal abcess. Cyrosurgery (i.e., application of a metal probe cooled by liquid nitrogen or carbon dioxide) freezes hemorrhoids. Occasionally, local anesthesia is required because of pain. Complications may include imprecise control of the depth of tissue destruction, post-operative pain, and rectal drainage. Surgical excision of hemorrhoidal inflammatory disease has the advantage of removing all associated redundant tissue, including the external component of a particular internal hemorrhoid. However, there are limitations to the amount of excision possible without major adverse sequelae. In a typical patient with many involved vessels, surgery can only approach the most symptomatic-diseased area and is not to be considered curative. The disadvantages of these approaches include pain, expense associated with hospitalization, time of disability, and potential complications, e.g., those associated with anesthesia, surgery proper, and post operative complications, including anal stenosis.

SUMMARY OF THE INVENTION

According to one aspect of the invention, an instrument for direct current electrical therapy of hemorrhoidal lesions or the like in a patient, comprises a D.C. electric generator means, a grounding pad for the patient, a monopolar probe having a distal tip for penetration of the hemorrhoidal lesion to act as a negative electrode, and an instrument handpiece for support of the probe and control of the level of direct current, the probe comprising a base and, extending therefrom, at least one elongated probe electrode terminating in the distal tip adapted for electricity-conducting engagement with a hemorrhoidal lesion, the instrument handpiece comprising a lower handle portion sized and constructed to be gripped by a physician, cooperative means for coupling the probe base to said handpiece in electricity-conducting engagement, with the axis of the probe at an obtuse angle to the axis of the lower handle portion, the obtuse angle selected to allow a physician to hold the instrument handpiece during treatment of a hemorrhoidal lesion without extended abnormal flexure of the wrist, therapy-monitoring and control upper handle portion disposed generally above the lower handle portion and having a front panel visible to the physician when the probe distal tip is penetrated into a hemorrhoidal lesion, the front panel comprising means for display of status of treatment conditions of the instrument, the means for display and the distal tip of the probe disposed generally in the same line of sight of a physician holding the lower handle portion with the distal probe tip penetrated into a hemorrhoidal lesion, and means for control of the level of direct current disposed adjacent the lower handle portion in a manner to allow a physician to operate the means for control with digits of a hand gripping said lower handle portion, whereby a physician may simultaneously view a treatment site and observe conditions of treatment appearing on the means for display, while gripping the instrument and operating the means for control with one hand, leaving the other hand free as he conducts therapy on a hemorrhoidal lesion.

Preferred embodiments of this aspect of the invention may include one or more of the following features. The means for display of status of treatment conditions of the instrument includes means for display of, e.g., elapsed time of treatment, means for display of status of treatment conditions of direct current intensity of treatment, and/or actuation status of treatment. The means for control comprises first means for increasing the level of current, and second means for decreasing the level of current, and may further comprise third means for ceasing direct current, preferably the third means being actuated by simultaneous actuation of the first and second means. The obtuse angle is of the order of about 120°. The cooperative means comprises the probe base comprising a key of predetermined size and shape, and a keyway defined by the instrument handpiece of size and shape to receive the key therewithin. Preferably, the key, taken in cross section, has the general form of a square with radiused corners of predetermined dimension corresponding to, but slightly less than, dimensions of the keyway. The probe is replaceable and comprises at least two elongated probe electrodes disposed in parallel array, preferably at least two distal tips of the elongated probe are longitudinally offset from each other.

According to another aspect of the invention, a probe adapted for use, e.g., with a hemorrhoid treatment instrument as described above comprises a base and, extending therefrom, at least one elongated monopolar probe electrode terminating in a distal tip adapted for electricity-conducting engagement with a hemorrhoidal lesion, and the probe further comprises cooperative means for coupling the probe base to the handpiece in electricity-conducting engagement, with the axis of the probe at an obtuse angle to the axis of the handpiece, the obtuse angle selected to allow a physician to hold the instrument during treatment of a hemorrhoidal lesion without extended abnormal flexure of the wrist, the probe base comprising a key of predetermined size and shape, and a keyway defined by the instrument handpiece being of size and shape to receive the key therewithin, the key, taken, in cross section having the general form of a square with radiused corners of predetermined dimension corresponding to, but slightly less than, the dimensions of the keyway.

The device of the invention offers a number of advantages over prior art approaches, including that it is effective, relatively safe and painless, and is cost containing, when compared to other methods of curative treatment of hemorrhoidal disease.

These and other features and advantages of the invention will be apparent from the following description of a presently preferred embodiment and from the drawings.

PREFERRED EMBODIMENT

We first briefly describe the drawings.

Drawings

FIGS. 4, 4A and 4B are diagrammatic views of the instrument of the invention during treatment of a hemorrhoidal lesion, taken from different perspectives;

FIG. 5 is a plan view of the instrument probe, while FIG. 5A is an end view of the probe base segment taken at 5A—5A of FIG. 5;

FIG. 5B is a plan view of an alternate embodiment of an instrument probe of the invention and FIG. 5C is a sectional end view of a base segment of the probe of FIG. 5B, taken at 5C—5C;

FIG. 6 is a table of probe orientations of the alternative probe base segment;

FIG. 7 is a plan view of the instrument grounding pad;

Figure 1:
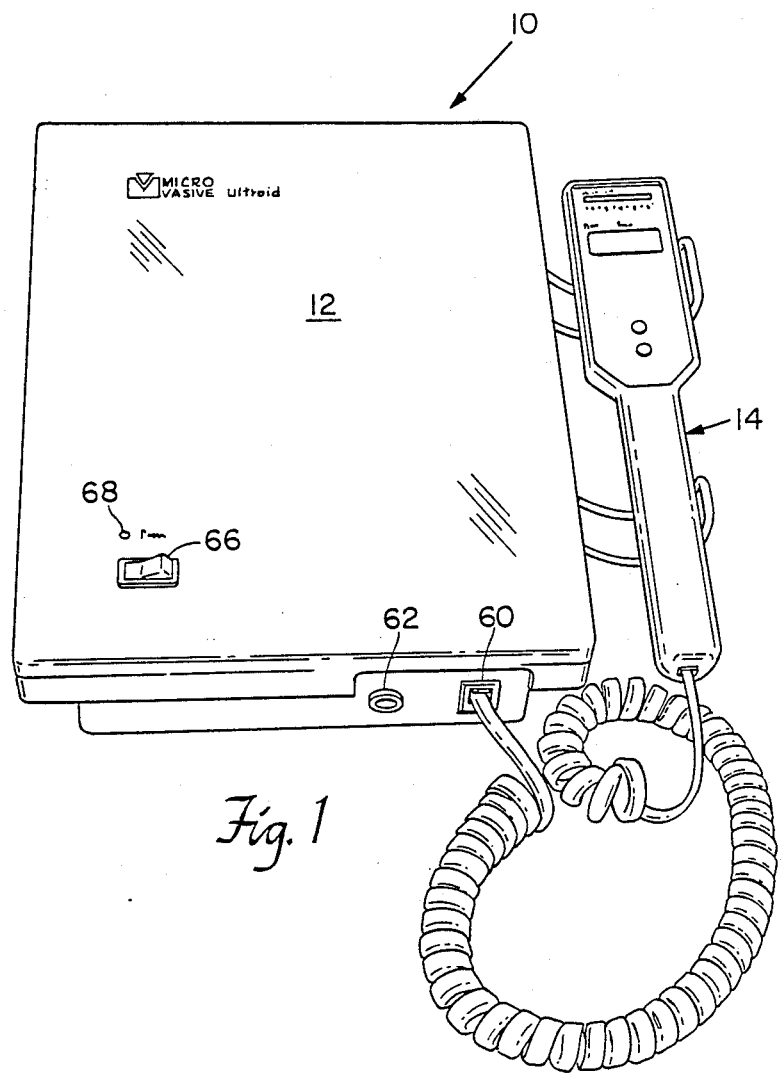
FIG. 1 is a perspective view of a medical instrument of the invention.

Referring to FIG. 1, the medical instrument 10 of the invention consists of a base unit 12 and a medical treatment handpiece 14. The instrument further consists of a monopolar, detachable probe 16 (FIG. 5) and a grounding pad 17 (FIG. 7).

Figure 2:
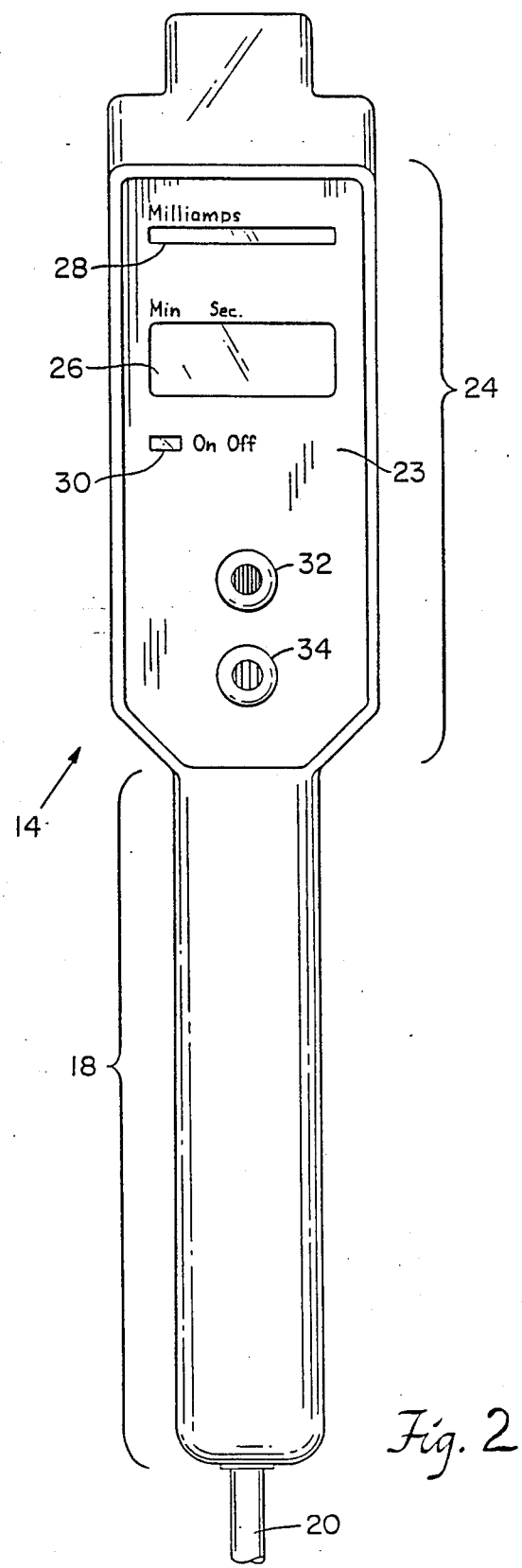
FIG. 2 is a plan view of the handpiece of FIG. 1.
Figures 3, 3A:
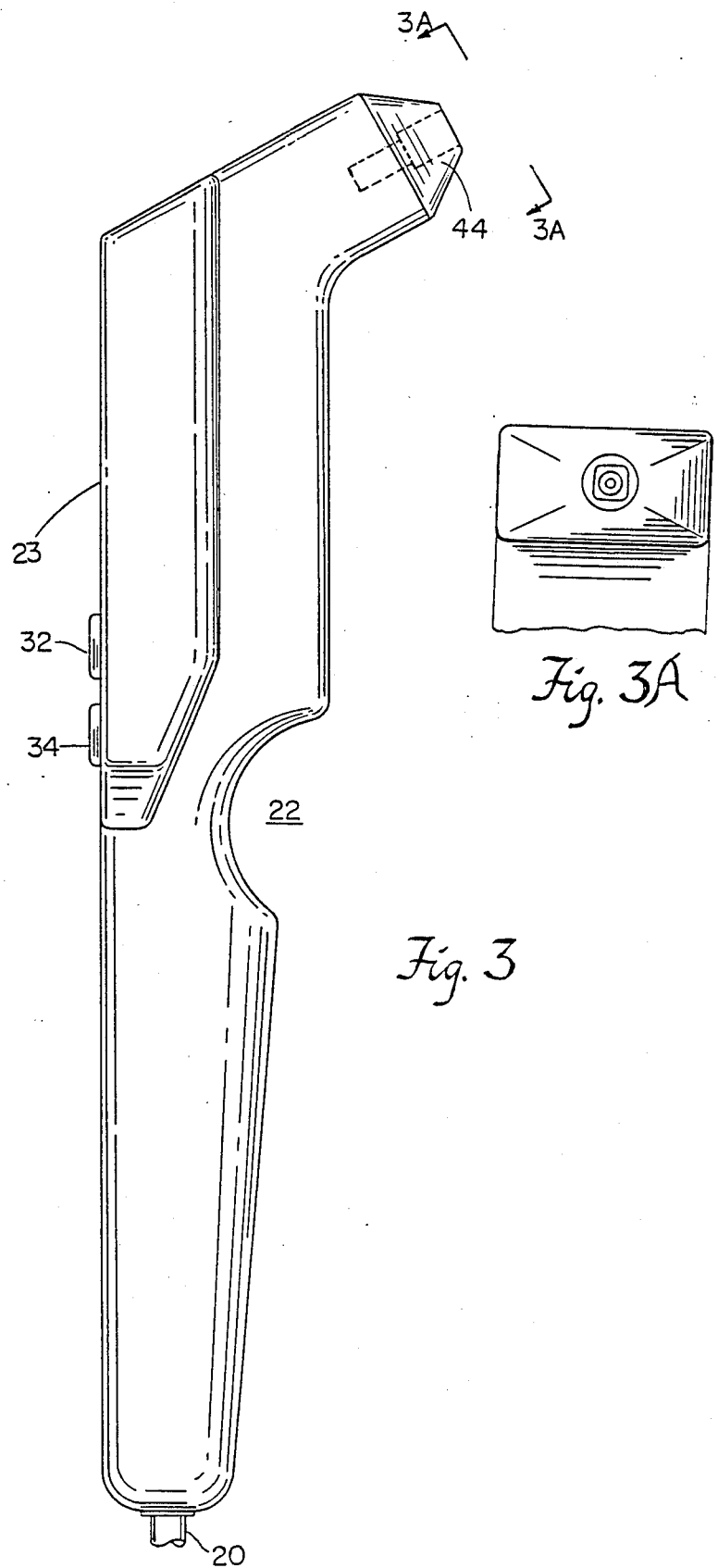
FIG. 3 is a side view of the handpiece of FIGS. 1 and 2.
FIG. 3A is a plan view of the probe receptacle of the handpiece of FIG. 3, taken at 3A—3A of FIG. 3.

Referring to FIGS. 2 et seq., the handpiece 14 consists of a lower handle portion 18 from which extends a connector cord 20 to the base unit 12, and, as shown in FIG. 3, includes a rear indentation 22 for receiving the fore finger of the user in gripping engagement. The planar face surface 23 of the handpiece, on the upper patient treatment portion 24, contains display elements of, e.g., elapsed time of treatment (LED numeric display 26), level of treatment current (LED bar graph 28), and circuit status indicator (on/off display 30). The upper patient treatment portion further contains switches 32, 34 for respectively incrementally increasing and decreasing the level of D.C. current through the probe and, when activated by the surgeon simultaneously, e.g., by pressing with his thumb, as described below, for ceasing flow of electricity. The handpiece face surface 23 is sealed against entry of fluid into the handpiece during cleaning between procedures.

Referring to FIGS. 4, 4A, 4B, 5 and 5A, the probe 16 consists of a pair of elongated, electrically-conductive electrodes 36, 38 extending to sharpened distal tips from a keying block 41, e.g., of square cross-section with radiused corners (FIG. 5A), sized to fit snugly within the aperture 40 (FIG. 4) provided in the distal end 44 of handpiece 14. A banana 43 plug adjacent to the keying block 41 firmly mounts the probe 16 to the handpiece 14. The probe electrodes are clad in nonconductive sleeves 46 over their distal portions to prevent inadvertent tissue contact, but to minimize obstruction to the surgeon's view of the treatment site. The proximal portions of the electrodes are encased in sleeve 48, e.g., of injection molded plastic. The probe base segment is constructed to be received into the aperture at four orientations (90° rotations), selected by the surgeon depending upon the rectal quadrant to be treated. Alternately, a probe 16′ (FIG. 5B) has a base segment 41′ of octagonal cross-section (FIG. 5C) fitted to the probe base segment. (A table of the alternate probe orientations is shown in FIG. 6C.) The tip element of one electrode 36 of the pair extends longitudinally beyond the tip element of the second electrode 38, whereby during treatment, the tips do not penetrate the tissue simultaneously, for reduced patient discomfort. For ease in manufacturing, the probe 16 may alternately be made with a simple, smooth sleeve 48 encasing the proximal portion of the electrodes, and the functions of the base segment and banana plug connector combined in the octagonal connector 41′.

The axis, P, of the probe, in assembly with the handpiece, extends at an angle, A, preferably about 120°, to the plane of face surface 23 of the handpiece. In this manner, during treatment of hemorrhoids, the distal tip elements of the probe are in contact with the hemorrhoidal tissue 50, and the important display elements on the patient treatment portion of the handpiece are both immediately along the line of sight, L′, of the surgeon 52′, allowing him to constantly observe the treatment site 54 and the treatment parameters, without turning away from the patient 56.

Figure 8:
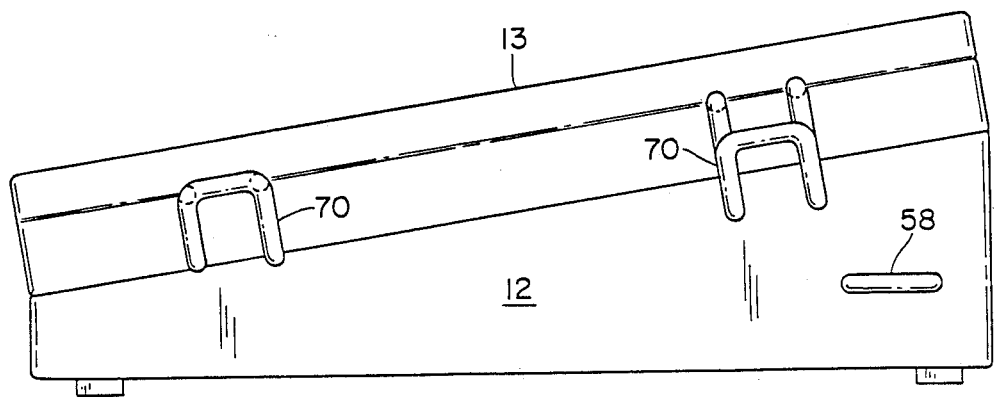
FIG. 8 is a side view of the instrument base unit.

Referring again to FIG. 1 and to FIG. 8, the base unit 12 includes a power cord 58 for connection of the instrument to a source of A.C. power and has outlets 60, 62 for connection of the handpiece cord and for connection of the cord 64 to the grounding unit 17 (FIG. 7). On the face surface 13 of the base unit 12, there is an on off switch 66, and a light element 68 for indicating actuation of the instrument. Extending from the side of the base are a pair of brackets 70 for receiving the handpiece.

The grounding unit 17 (FIG. 7) consists of an absorbent pad 72 within a liquid impervious container 74. Power cord 64 connects the grounding unit to the base unit at outlet 62.

Figure 10:
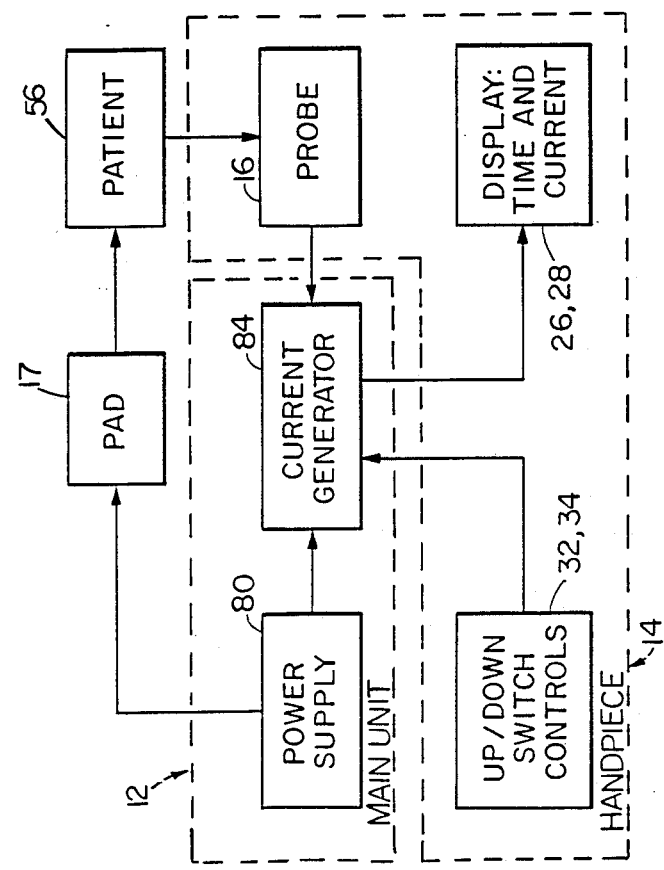
FIG. 10 is a block diagram of instrument circuitry.

Referring to FIG. 10, the medical instrument consist of three electrical components; a main unit 12, a hand piece 14 and a pad 17. The main unit is comprised of a power supply 80 and a current generator 84. The power supply 80 provides D.C. voltage to logic circuitry of the switch controls 32, 34, the time and current display 26, 28 and the ground pad 17. The current generator 84 is connected to the probe 16 and is used for controlling electrical D.C. current that is to be transmitted from the pad 17 through the patient 56 to the probe 16. In handpiece 14, switches 32, 34 positioned on the handle of the probe are connected to the current generator 84 for incremental adjustment of the current transmitted through the patient 56. Digital circuitry components, connected to the current generator 84 and placed on the handle of the probe, enable a visual display 26, 28 of the quantity of current transmitted and elapsed time of treatment.

Figure 11:
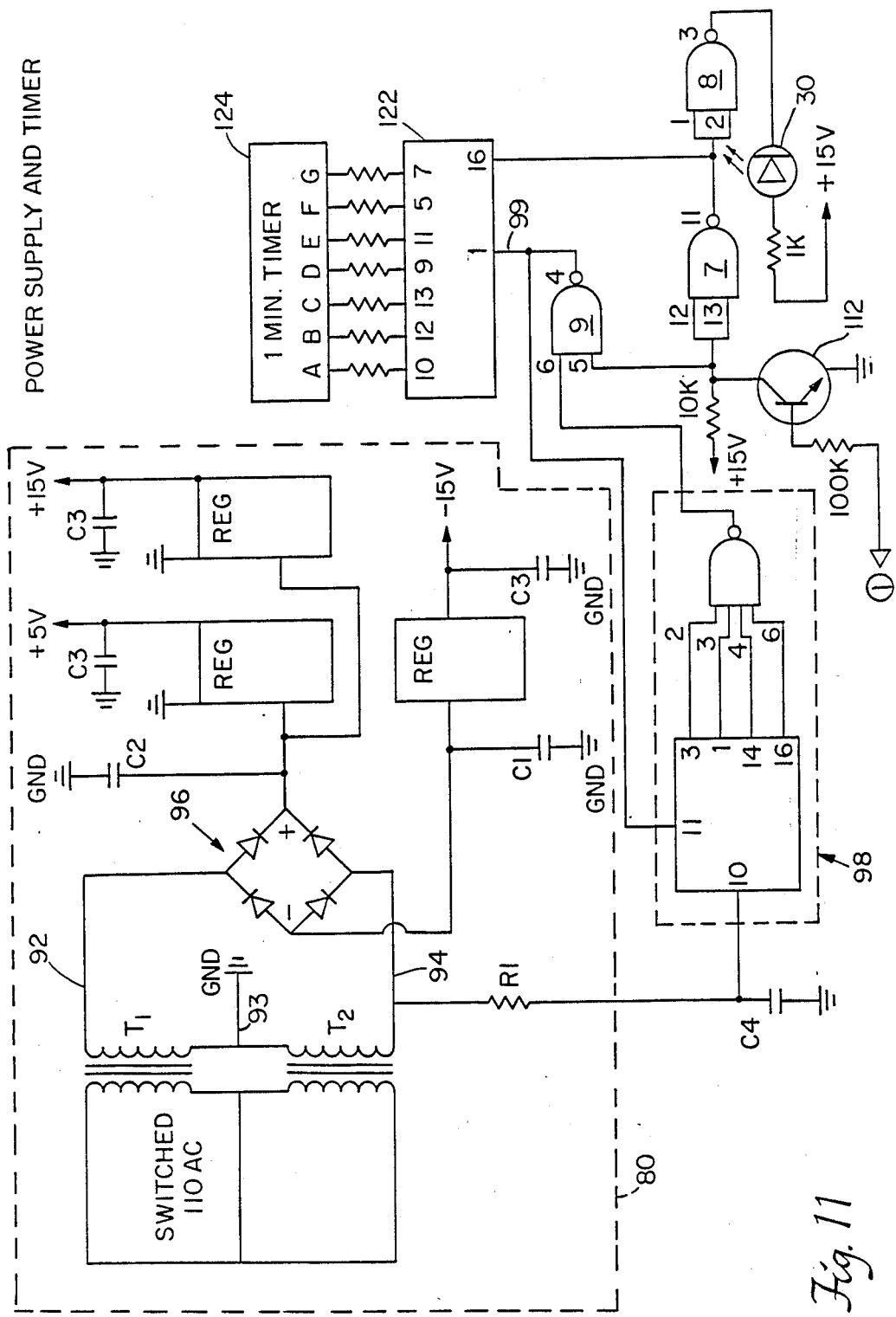

Referring to FIG. 11, the power supply 80 consists of two 110 v to 25.2 v step-down transformers $T_1$ and $T_2$ wired in series. The common connection 93 on the secondary side is connected to ground and the two remaining secondary leads 92, 94 provide a total potential of 50.4 volts A.C. when used together or 25.2 volts A.C. from each lead to ground (the same as a simple 110 v to 50.4 v center tap transformer). The A.C. voltage is converted to D.C. by the use of a bridge rectifier 96 and is filtered by two 1000 uf capacitors $C_1$ and $C_2$ connected to ground. This circuit provides a positive 35.6 volts and a negative 35.6 volts power supply on leads 92 and 94, and is known as a split voltage supply. The voltage increase (from 25.2 volts to 35.6 volts) is due to the configuration of the power supply and its capacitors. Three voltage regulators (REG) are used to provide three regulated voltage supplies: +15 volts; −15 volts; and +5 volts. Each of these regulators are filtered by a 0.1 uf capacitor $C_3$. The +15 volts is applied to the pad 17 and the +5 volts is applied to the electronic circuitry discussed below.

A one megohm resistor $R_1$ in series with an 18 uf capacitor $C_4$ taps off the 25.2 volt A.C. supply to provide a 60 hz signal for a one minute timer section 98. The timing circuit 98 divides the 60 hz by 3600 thus giving a one pulse/minute signal 99 to a driver chip 122, which is capable of counting from zero to seven. The driver chip 122 turns on and off seven LED segments of an LED display 124, which digitally indicates the number of minutes of treatment. The LED display 124 is reset to digitally show "0" when the current generator 84 (FIG. 10) is reset or a new treatment is initiated (discussed below).

Figure 12:
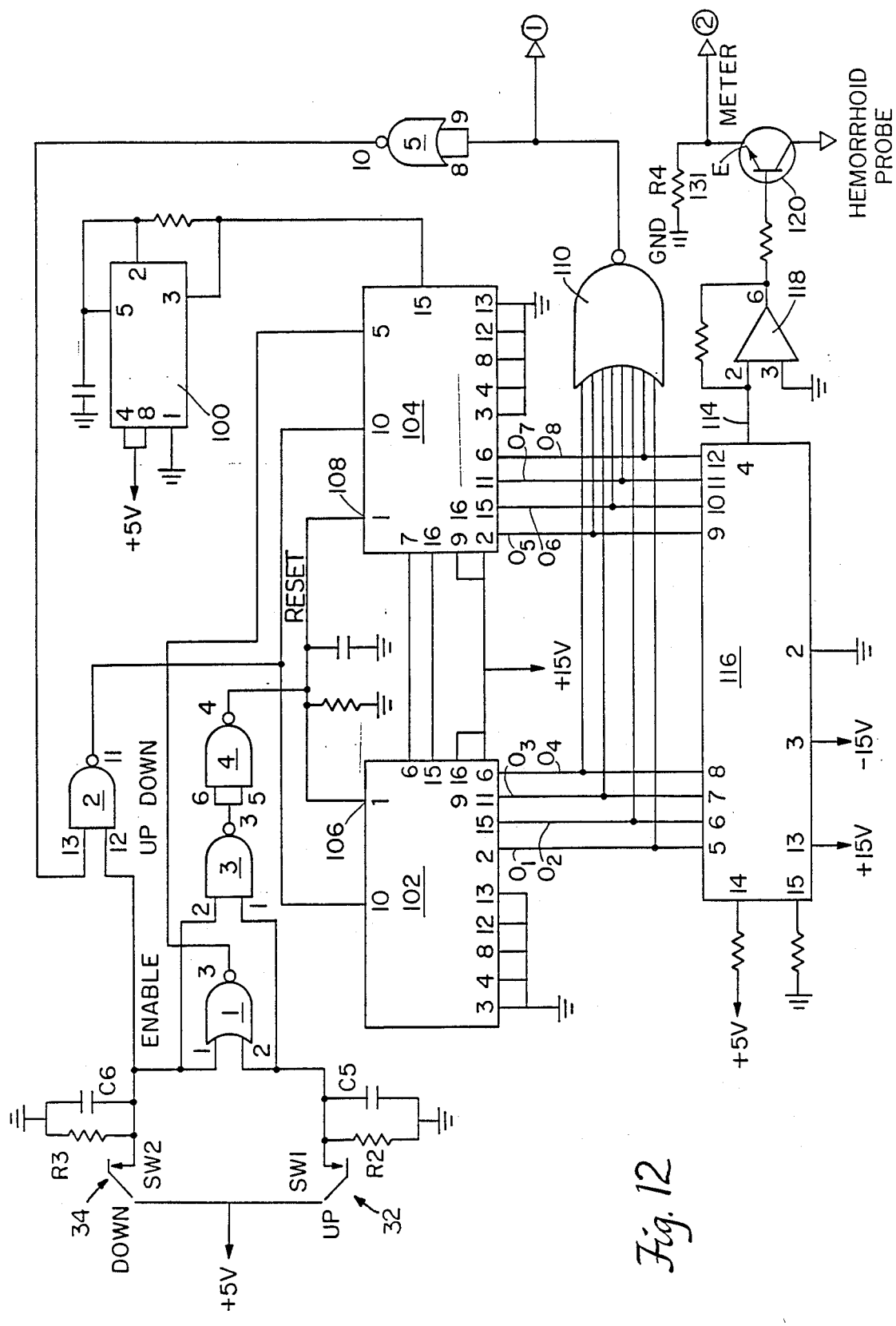

Referring to FIG. 12, the current generator 84 contains: a pulse generator 100; logic gates 1-6; a counting circuit 102 and 104; a digital-to-analog voltage converter 116; and a current driver 120.

The pulse generator 100 provides a constant two hz/second square wave output which feeds into the two 4-bit binary counters, 102 and 104, operating in effect as one 8-bit binary counter. Switches 32 and 34, located on the probe handle (see FIG. 2), apply a positive voltage to logic gates 1-4 which in turn determine three possibilities:
1. Tells the counter to count up (Gate 1);
2. Tells the counter to count down (Gates 1 and 2); or
3. Resets the counters (Gates 3-4).

In other words, when switch 32 is depressed to make electrical contact with the +5 voltage supply, the counter is told to count up via gate 1. When switch 34 is depressed, the counter is told to count down via gates 1 and 2. Pressing both switches 32 and 34 simultaneously causes the counters 102, 104 to be reset. Preferably, the timer 124 (FIG. 11) is also reset when both switches 32 and 34 are pressed. A one megohm resistor, $R_2$, $R_3$, in combination with a parallel 0.1 uf capacitor, $C_5$, $C_6$, which tie each switch, 32 and 34 to ground, are used to pulse the resets 106 and 108 on the counters via gates 3 and 4 when the unit is turned on.

The counter 106, 108 has outputs $O_{1-8}$ which operate cooperatively to provide a digital count of up to 256. The outputs of the counters are applied to an eight input digital-to-analog converter 116. As the counter increments or decrements the count, the digital-to-analog converter 116 increases or decreases its output voltage 114 proportionately to the output count of the counters. The output voltage 114 of the digital-to-analog converter 116 is fed to an operational amplifier 118 which acts as a buffer and multiplies the output voltage 114 to drive a npn transistor 120. Transistor 120 provides a current sink from the patient to ground. In other words, the probe acts as a current return from the pad 17, which provides the positive voltage source, to the system ground (GND). The current flow is limited by a 131 ohms resistor $R_4$ in series with the emitter E of the transistor 120.

A twelve volt bulb (not shown) may be provided at the tip of the probe for providing light for the examination of a patient. This bulb may be driven by the 15 volt negative source (FIG. 11) to provide high intensity light.

In order to protect the patient from a large, sudden application of D.C. current, the outputs of the counters are also applied to an eight input NOR gate 6 which is used (with gates 5 and 2) to prohibit the counters from continuing a backward count when the counter reaches 0000 0000.

Referring again to FIG. 11, the output of NOR gate (FIG. 12) is used to control the one minute timer and a green LED, 30, which indicates the electrical status of the unit. When the count of the counters 102 and 104 equals 0000 0000, a positive voltage is applied to transistor 112 from gate 6 over line 113 causing it to conduct current. As a result of logic gates 7-9, the driver chip 122 is reset and the green LED, 30, is enabled.

Figure 13:
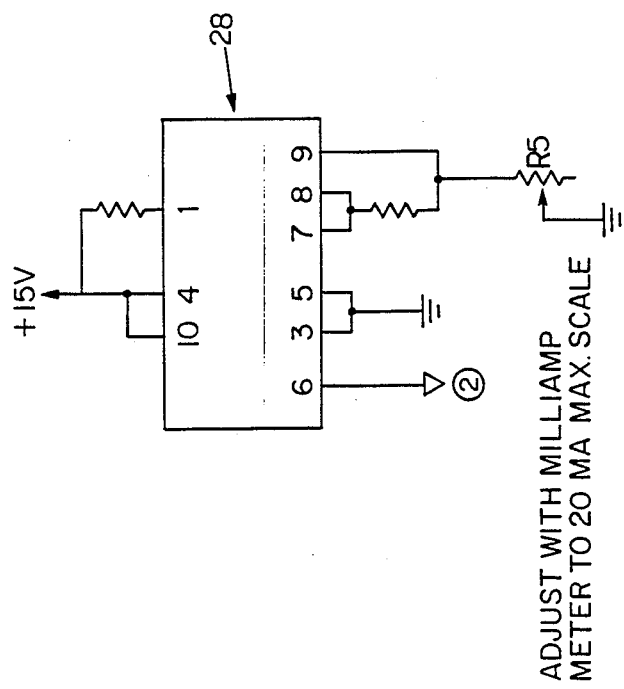
FIGS. 11, 12 and 13 are schematic diagrams of a first embodiment of the electrical circuitry of FIG. 10.

Referring to FIG. 13, a current indicator 28, is connected to the emitter E of the transistor 120 via line 115. The current indicator, using Ohm's law, indicates the amount of current passing through the patient by measuring the voltage across the 131 ohm resistor $R_4$ (FIG. 12). The amount of current transmitted through the patient is displayed by a bar graph array. Preferably the indicator 28 is calibrated to a 20 mA maximum scale by a 10,000 ohm variable resistor R5.

Figure 14:
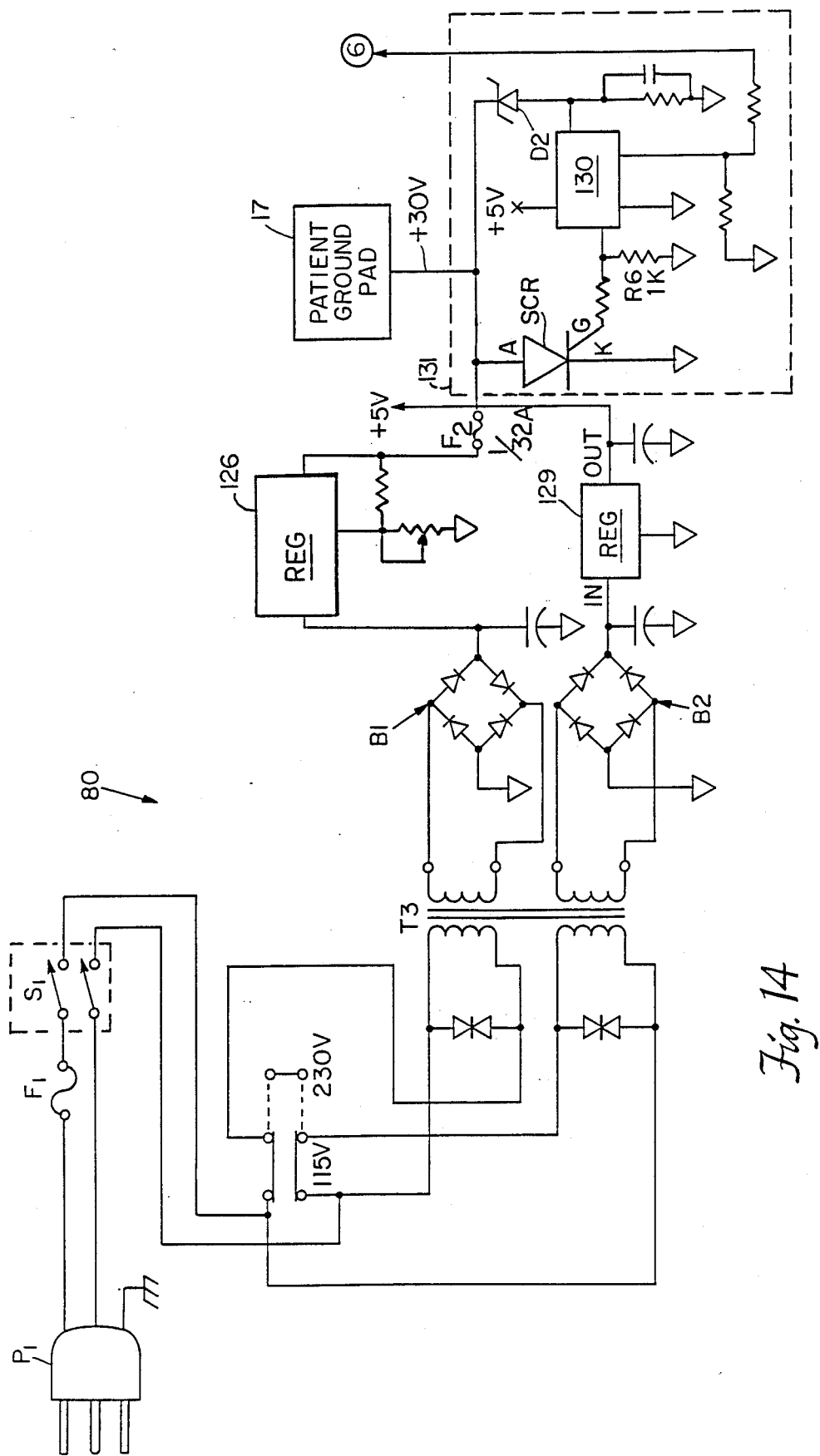
FIGS. 14 through 16 are schematic diagrams of a second embodiment of the electrical circuitry of FIG. 10.
Figure 15:
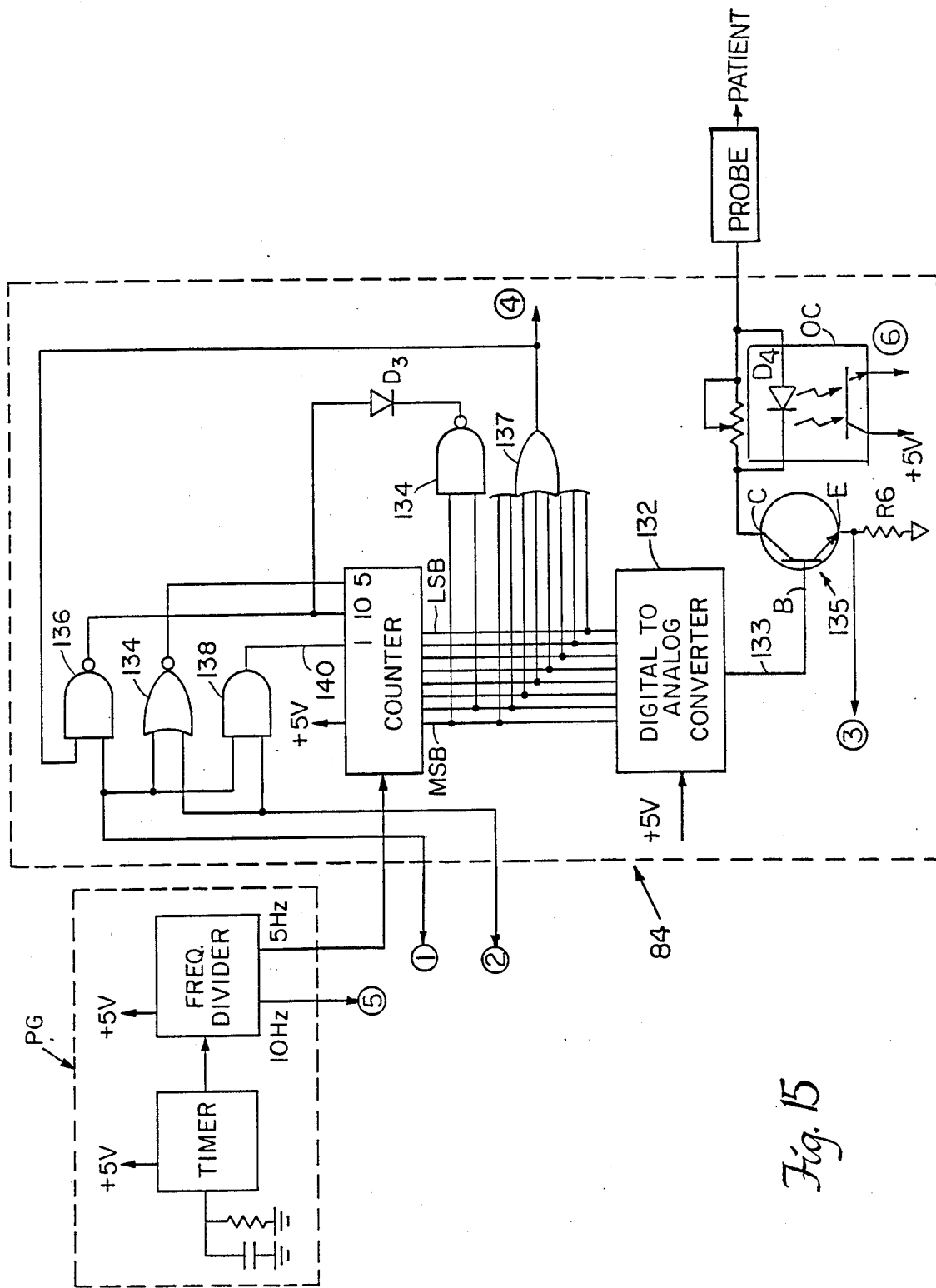
Figure 16:
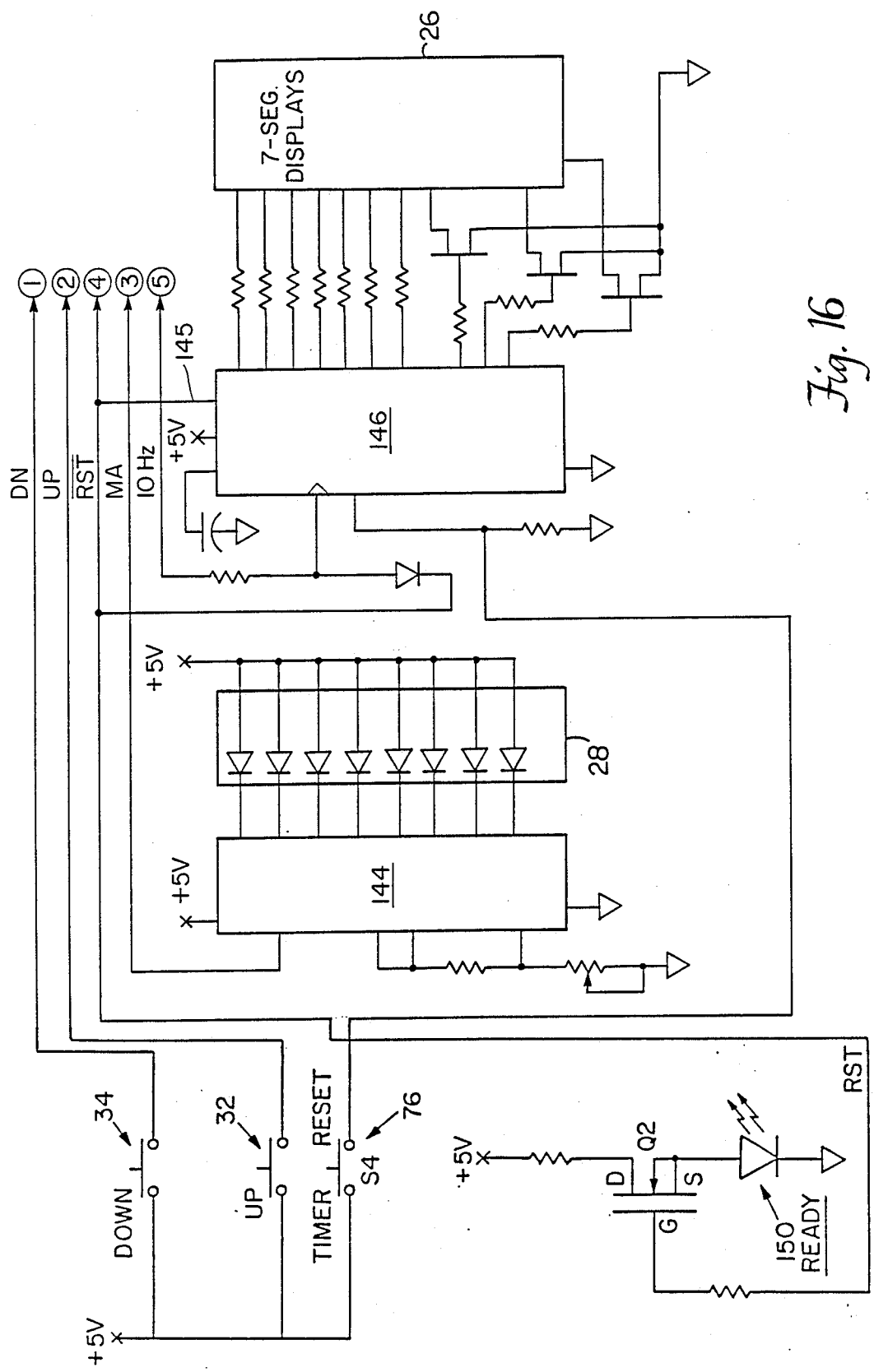

Referring to FIGS. 14, 15, 16, an alternate schematic diagram is shown. The power supply 80 is comprised of a transformer $T_3$ and two bridge networks $B_1$ and $B_2$, which convert either 115 VAC or 230 VAC from an electrical outlet into 5 volt D.C., labeled +5V, and 30 volts D.C., labeled +30V, power supplies. The 5 volt DC power supply, +5V, is regulated by a voltage regulator 129 and is used to power the logic circuitry used in the medical instrumentation. The 30 volt D.C. power supply is also regulated by a voltage regulator 126 and is used for supplying a positive potential to the ground pad 17. Generally, the regulator 126 will protect the patient from power surges, but for extra caution, a fuse F2 is connected in series with a supervisory circuit 131. Preferably the fuse limits the current to 1/32 amperes. The supervisory circuit 131 causes the fuse to blow if there is a voltage surge on the 30 volt line. At that point, a zener diode D2 conducts current, which in turn causes the supervisory circuit to fire a silicon-controlled rectifier (SCR) thereby shorting the +30V power supply to ground and blowing the fuse. The supervisory circuit 131 similarly detects an excessive current transmitted by the probe via line 82 from an optical coupler, OC, (FIG. 15).

Referring to FIG. 15, the amount of D.C. current applied to the patient is controlled by the current generator 84. The current generator 84 includes an 8-bit digital counter 139 which is driven incrementally by a pulse generator (PG). The pulse generator also drives a display circuit described below. The digital output count of the counter 139 is fed to a digital-to-analog converter 132 which supplies an output voltage 133 that is directly proportional to the output count of the counter 139. The output voltage 133 is then applied to the base (B) of a transistor 135 which provides a current sink from the patient to ground. The amount of current transmitted through the probe is controlled by the amount of voltage applied to the base (B) of the transistor 135. Thus, as the digital count increases, the D.C. current transmitted through the probe increases.

Circuitry is provided which limits the amount of voltage applied to the base, B, of the transistor 135. The output of a NAND gate 134, which is connected to the two most significant bits of the counter, is fed through a diode (D3) back to the counter 139 for the purpose of establishing a terminal count. The terminal count prevents a sudden step of current to the patient when the counter cycles from its maximum value to its minimum value during a directive to count up. If a terminal count were not provided, the severe drop in the applied current would cause discomfort to the patient.

Referring to FIG. 16, the voltage at the output of the digital-to-analog converter is controlled by an "up" switch 32 and a "down" switch 34 on the handle of the probe. Both switches 32 and 34 are connected at one end to the 5 volt output, labeled +5V, power supply. At the other end, the switches 32 and 34 are connected to logic gates 136, 137, and 138 (FIG. 15) by lines 88 and 89 respectively. Opening and closing switches 32 and 34 generate output signals which control the output count of the counter 139. By depressing only switch 32, the counter 139 is told to count up to a maximum count established by the predetermined terminal count. By depressing only switch 34, the counter is instructed to decrement the count to a minimum count of 0000 0000 which is a digital zero count. As discussed above, this prevents the counter from cycling back to a maximum count, which would cause a maximum amount of current to be transmitted through the probe. When both switches are depressed simultaneously, the counter 139 is reset. A display of the amount of current applied to the patient is indicated by a bar graph display 28, which is located on the probe handle. The bar graph display is driven by an analog-to-digital converter 144, which detects the voltage at the emitter E of the transistor 135 via line 143. The analog-to-digital converter produces a digital signal which is proportional to the voltage detected at the emitter E. It is preferred that the analog-to-digital converter 144 supply outputs for firing eight separate light-emitting diodes (LED), each of which represent two milliamps on the bargraph display. Thus, when all the LEDs are lit, sixteen milliamps or full scale will be represented.

A digital display 26 for indicating the amount of time elapsed for applying current to the patient is also provided on the probe handle. A digital clock driver 146 which may be a counter is clocked by a 10 hertz signal over line 143 from the pulse generator PG (FIG. 15). The output count of the counter 146 is used to drive three 7-segment digital displays, which represent minutes and seconds During treatment, the 7-segment digital displays keep track of the amount of time that a patient has received D.C. current. If the current transmitted by the probe is reduced to zero, a signal 145 indicative of a digital zero count as applied to the digital-to-analog convertor 132 is applied to the counter 146 for latching the time displayed. In other words, time shown on the clock will stop and indicate the elapsed treatment time when the current is reduced down to zero. When current is again applied to the patient, the time shown on the clock will continue.

Handpiece 14 may also include a display which indicates whether the probe is electrically active for transmitting current. When the output count of the counter 139 is other than a logic zero (i.e. the probe has the potential to transmit current), line 150 enables a red LED 151 via gate $Q_2$.

Figure 9:
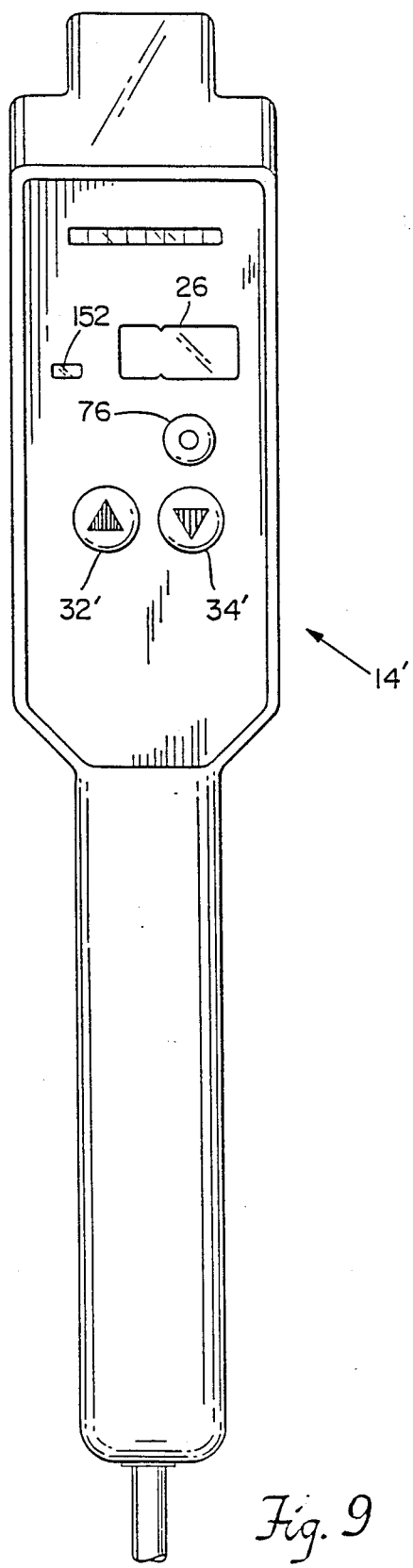
FIG. 9 is a face plan view of an alternate embodiment of the instrument handpiece.

Referring to FIG. 9, in an alternate embodiment of the handpiece 14, in order to reset the time on the display, a reset switch 76 may be provided. Also, in this embodiment, the "up" and "down" switches 32, 34' are disposed in side-by-side relationship.

The instrument is assembled by inserting the base segment 41 of a new probe 16 into the aperture 40 of the handpiece 14. The handpiece and grounding pad connector cords 20, 64 are inserted into their respective outlets 60, 62, and the base unit is connected to a source of A.C. power via cord 58.

The patient 56 is positioned in a right lateral fetal position, with the grounding pad 17, moistened with saline for good electrical contact, acting as the positive electrode, positioned under the patient's right thigh. The surgeon inserts and positions an anoscope 51 to expose to view through a window 53 a hemorrhoid 50 to be treated. The surgeon depresses switch 66 on the base unit 12 to actuate the instrument, as indicated by light 68. At this point, display 30 on the handpiece indicates that the circuit is not closed. The surgeon engages the base of the hemorrhoidal lesion with the tips of the electrodes 36, 38 of the probe 16, indicated as a closing of the circuit (from the grounding pad through the patient to the electrode tips) by display 30. The surgeon incrementally increases current through the probe by depressing switch 32, with the level of current indicated by the bar graph 28, and the elapsed time of treatment indicated by display 26. As current is initiated, the surgeon urges the probe tips into the base of the lesion. It has been observed that the degree of treatment required is a function of time and current, i.e., the higher the level of current, the shorter the time required for each treatment procedure. The factor limiting current intensity is patient discomfort; the surgeon, there-fore, by depressing switch 32, slowly increases the level of current as high as possible without patient discomfort (experienced as an aching feeling) in order to shorten the time of treatment. Should the patient feel discomfort, or when the treatment is completed, the surgeon reduces the current incrementally by depressing switch 34.

Figure 4:
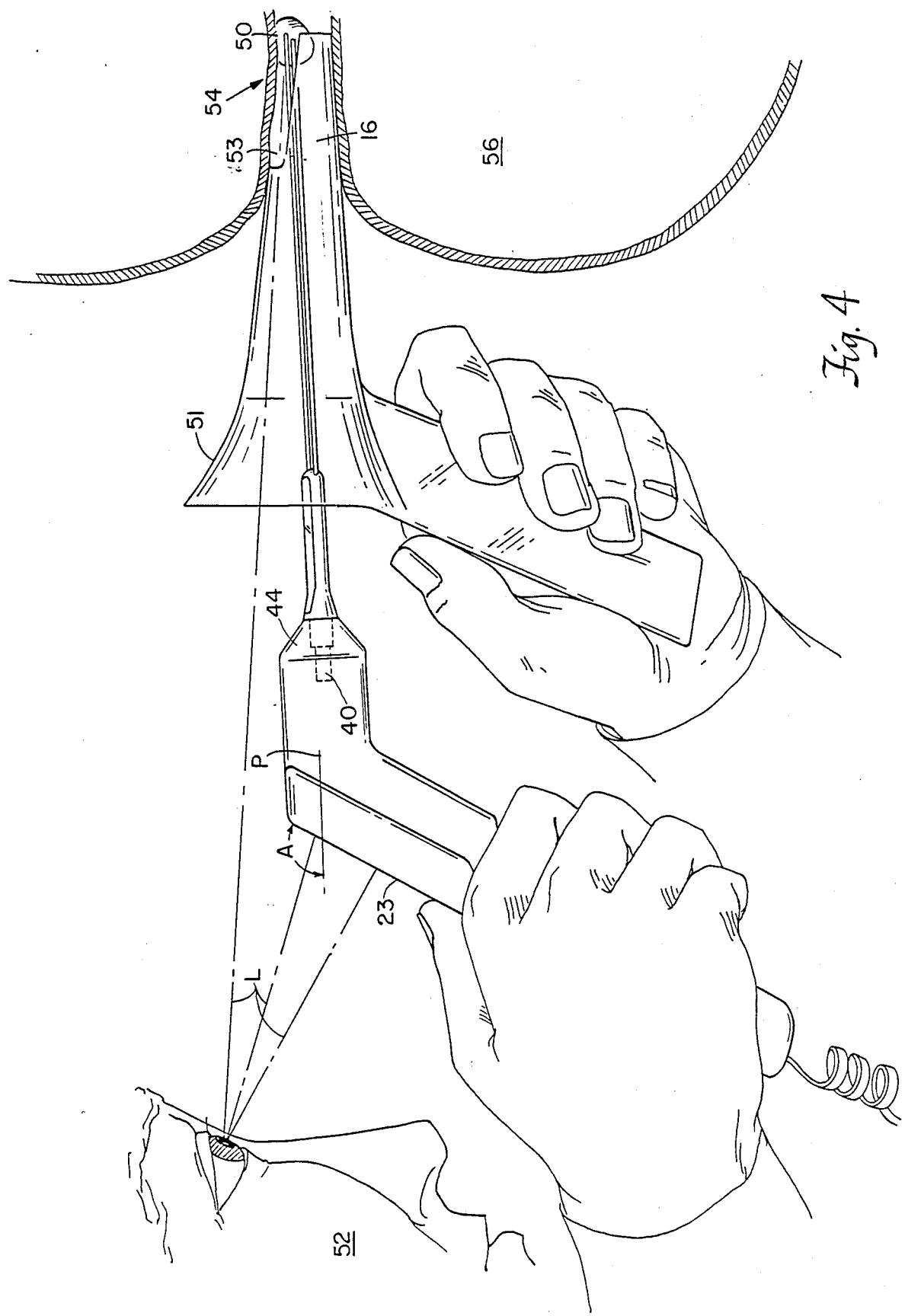
Figure 4B:
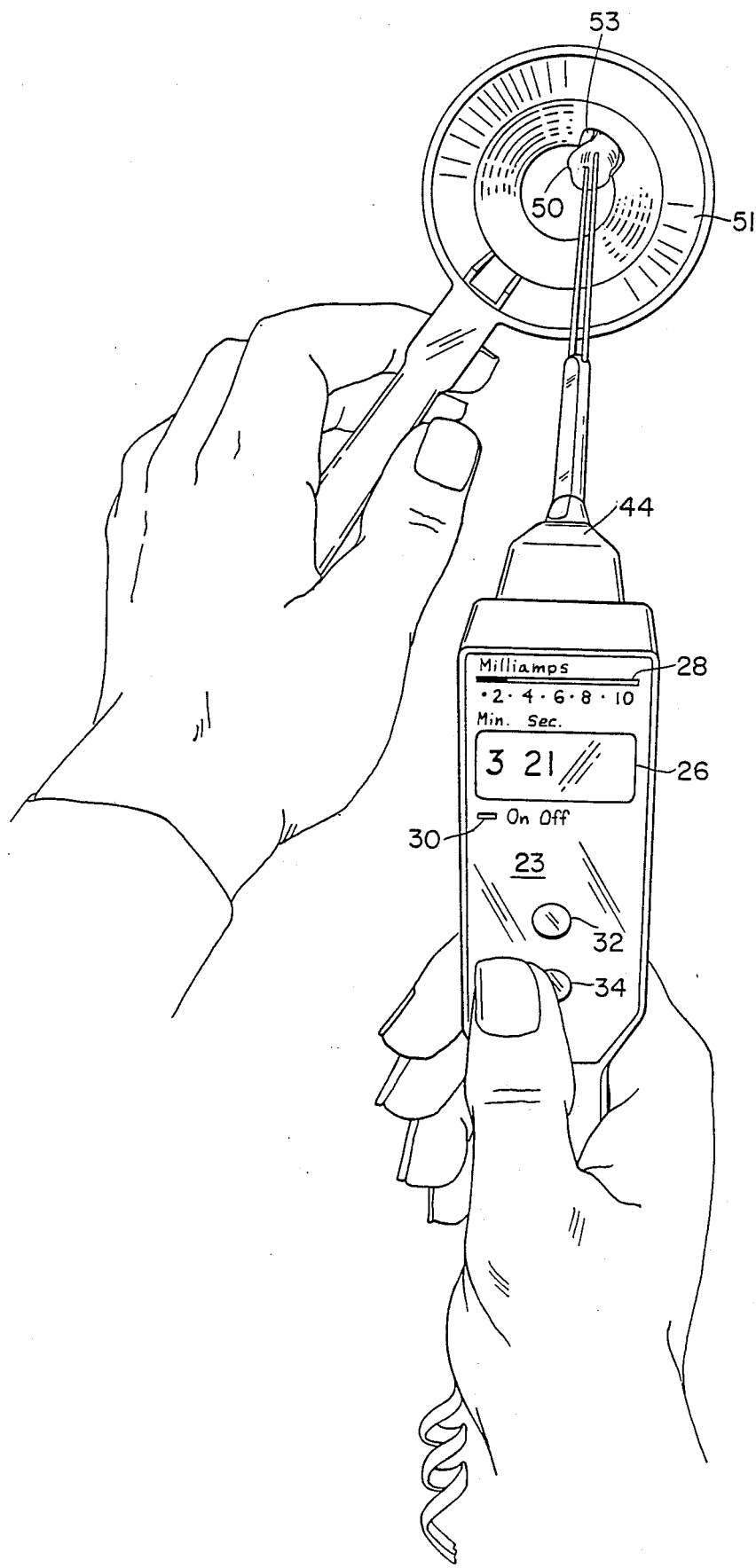

The length of each treatment period may typically be in excess of 5 or 10 minutes, but the configuration of the handle portion of the handpiece and the axis of the probe, best seen in FIGS. 4, 4A and 4B, allows the surgeon to position his wrist comfortably, without abnormal flexure. Furthermore, as described above, the relative arrangement of the displays of conditions of treatment and the probe tip elements relative to the surgeon's line of sight allows him to simultaneously monitor the status of the patient and the conditions of treatment.

Results:

Forty-two patients with symptomatic hemorrhoidal disease were treated with a device of the invention. The group consisted of 28 males and 14 females with a mean age of 47 (range 21-70 years).

All subjects underwent historical review, visual and digital examination, and anoscopy utilizing the Hinkle-James Rectal Speculum. Subjects with source other than hemorrhoidal disease accounting for their symptomatology were not included in the study.

At anoscopy, eight segments were visualized. With the patient in the right lateral position, segment 1 is on the patient's left and segment 6 is on the patient's right anterior. Hemorrhoidal inflammatory disease was graded from 0-4 according to Banov et al. Grade 0 represents no abnormality. Grade 1 represents tuft or internal hemorrhoidal tissue present but no prolapse from the anal canal. These produce painless bleeding. Grade 2 represents prolapse with straining, and tissue retracts after the bowel movement. The patient may be unaware of the prolapse episode. Like Grade 1, Grade 2 hemorrhoids may bleed. Grade 3 represents prolapse of the hemorrhoidal tissue with a bowel movement, and the hemorrhoids remain out. The patient has to replace them manually. Grade 3 hemorrhoids may bleed or have associated pain. Grade 4 represents hemorrhoid prolapse that is unable to be reduced, often with associated mucoid discharge and bleeding.

Each patient underwent treatment of all internal hemorrhoids with inflammatory change. Most hemorrhoids required a single treatment which was recorded as milliamperes (ma) applied times minutes of application (ma×min). In general, one treatment would be given per appointment; however, more than one small vessel would occasionally be treated at a single sitting. If on re-examination, total ablation of hemorrhoidal disease from a prior treatment was not obtained, additional treatment to that vessel would be given. This would be recorded as additional milliamperes and time of treatment.

A typical treatment consisted of visualization of the hemorrhoid to be treated utilizing the Hinkle-James Rectal Speculum. Treatment was directed at the uppermost portion of the hemorrhoid, in the longitudinal axis of the vessel and at a very slight angle to the rectal canal. If desired, this area was topically anesthetized with 4% Xylocaine utilizing a cotton tip swab. The probe was firmly inserted into the vessel lumen. The current was then turned on gradually, with two to three minutes being required to bring the current to 10 to 15 ma. Utilizing the dual tipped probe, 60 to 100 milliampere minutes of treatment was required per involved vessel. Visual changes of bright to dark red, and, in some instances, a nearly black color, indicated a satisfactory treatment course. The current was slowly turned off and the probe and speculum removed.

Forty-two patients, mean age 47 (range 21 to 70), underwent evaluation for symptomatic hemorrhoidal disease and treatment. The mean duration of symptoms prior to treatment was 9.7 years (range 0.01 to 26 years). Symptoms at presentation and number of treatments required for complete resolution of these symptoms are presented in Table I. The most common symptoms were rectal bleeding in 81% of patients, followed by pruritus (62%), internal hemorrhoid protrusion through the anal canal (60%) and pain (42%). The mean number of treatments for complete resolution of these symptoms, with one involved vessel treated per visit, was 2.0, 2.9, 2.9, and 2.8 respectively.

TABLE I

Symptoms and number of D.C. current treatments required for symptoms resolution in 42 patients with hemorrhoidal disease.

|  | PRURITUS | PAIN | BLEEDING | PROTRUSION |
|---|---|---|---|---|
| Symptom % of Patients | 62 | 42 | 81 | 60 |
| # Treatments (x) for Symptom Resolution | 2.9 | 2.8 | 2.0 | 2.9 |

The mean number of diseased hemorrhoidal vessels was 6.33 per patient. Hemorrhoidal vessel involvement is shown in Table II, the mean grade of inflammatory change being the greatest on the left and the least in the right anterior segment.

In the 42 patients, a total of 17 Grade 1, 103 Grade 2, 99 Grade 3, and 46 Grade 4 hemorrhoids were treated. The amount of milliamperes, time and milliampere-time product required for complete ablation of inflamed hemorrhoidal tissue is directly related to the degree of inflammatory change.

TABLE II

Hemorrhoidal Quadrants corresponding to mean inflammatory grade of hemorrhoidal involvement in 42 patients.

| Area | 1 | 2 | 3 | 4 | 5 | 6 | 7 | 8 |
|---|---|---|---|---|---|---|---|---|
| Grade | 2.8 | 1.8 | 2.5 | 1.9 | 2.3 | 1.2 | 2.2 | 2.0 |

All patients were asymptomatic at completion of the treatment course.

Patient follow-up was obtained in all patients by direct contact. Mean duration of follow-up was 18.2 months (range 8-34 months). No recurrence of symptomatology was reported at follow-up evaluation.

Mechanism of Treatment

The precise mechanism of action of D.C. Current to bring about resolution of hemorrhoidal inflammation without resulting scar tissue formation is not known. However, vessel thrombosis with eventual slough is the end result. When applied to hemorrhoids, the negative pole of D.C. Current produces a hydrolytic decomposition followed by a contraction of the tissues. Hydrolytic decomposition results in vessel thrombosis, with that of the vasa vasorum most probably paramount.

Two possible explanations for vessel thrombosis by the use of D.C. current are: the release of free hydrogen, i.e., when the probe is placed in a saline solution (such as blood) and current is passed, free hydrogen is produced; and production of heat at the site of the probe with the formation of hydrogen. Both explanations will cause the release of adenosine diphosphage (AIP) and/or thromboplastin.

The dried hemorrhoidal tissue sloughs gradually over a 3 to 7 day period, being eliminated with defecation. Hemorrhage associated with tissue slough has not been experienced. Follow-up evaluation reveals no evidence of scar tissue formation. The permanency of therapeutic effect is due to complete obliteration of the entire vessel from its point of origin to its most dependent portion.

Because the superior (internal) and inferior (external) hemorrhoidal vascular plexuses anastomose freely, many patients have a combination of hemorrhoids (mixed hemorrhoids) and likewise external hemorrhoidal inflammatory disease is resolved with D.C. Current treatment of internal hemorrhoidal disease.

The absence of pain with this procedure relates to the relative lack of somatic innervation of the area of origin of internal hemorrhoids. Should a patient have innervation above the Dentate Line, topical application of 4% Xylocaine allows for no greater than a tolerable discomfort during the treatment period.

These and other embodiments are within the following claims. For example, the base unit 12 may have brackets adapted to receive the assembled handpiece and probes, and may be wall mounted. The probe may have a multiplicity of electrode elements, the number, e.g., 1 or 3 or 4 or more, and pattern, e.g., in a polygon or curve or line or other pattern, selected on the basis of the shape and size of the base region of the hemorrhoidal lesion to be treated. The electrode elements may also be curved or bent to improve visibility or access to the lesion.

Figure 9A:
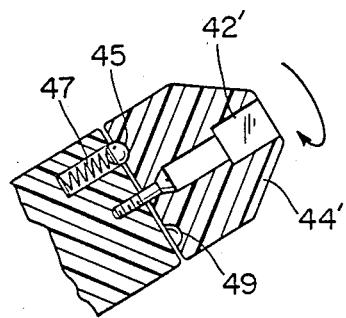
FIG. 9A is a sectional side view of the distal end of a handpiece of the invention having a rotatable tip.

Also, referring to FIG. 9A, the probe may be rotatable to a predetermined number of positions, e.g., by selection of corresponding shapes of keying block and handpiece aperture 42' (e.g., square or other shape), or to an infinite number of positions by rotation of handpiece tip 44' about a shoulder of a screw along the probe axis. For example, a ball 45 biased by a spring 47 against notches 49 formed in the tip 44' may be used for locking the position of the probe.

The instrument may be adapted for RF treatment of lesions, or may be used for treatment of other conditions, e.g., fissures.

Also, referring to FIG. 9 and as mentioned above, the increasing/decreasing element control switches 32', 34' may be disposed side by side, and a third switch 76 provided, e.g., for resetting the elapsed time of treatment counter 26. The handpiece or base unit may also include means for audio signals, e.g., of treatment time or current flow, or may include means for recording time or other conditions of treatment.

What is claimed is:

1. An instrument for direct current electrical therapy of hemorrhoidal lesions or the like in a patient comprises a D.C. electric generator means, a grounding pad for the patient, a monopolar probe having a distal tip for penetration of the hemorrhoidal lesion to act as a negative electrode, and an instrument handpiece for support of the probe and control of the level of direct current, said probe comprising a base and, extending therefrom, at least one elongated probe electrode terminating in said distal tip adapted for electricity-conducting engagement with a hemorrhoidal lesion, said instrument handpiece comprising:
  a lower handle portion sized and constructed to be gripped by a physician,
  cooperative means for coupling said probe base to said handpiece in electricity-conducting engagement with the axis of said probe at an obtuse angle to the axis of said lower handle portion, arrangement of said probe and said lower handle portion at said obtuse angle allowing a physician to hold said instrument handpiece during treatment of a hemorrhoidal lesion without extended abnormal flexure of the wrist,
a therapy-monitoring an control upper handle portion disposed generally above said lower handle portion and having a front panel visible to the physician when the probe distal tip is penetrated into a hemorrhoidal lesion,
said front panel comprising
  means for display of status of treatment conditions of said instrument, said means for display and the distal tip of said probe disposed generally in the same line of sight of a physician holding said lower handle portion with said distal probe tip penetrated into a hemorrhoidal lesion, and
  means for control of the level of direct current disposed adjacent said lower handle portion in a manner to allow a physician to operate said means for control with digits of a hand gripping said lower handle portion,
whereby a physician may simultaneously view a treatment site and observe conditions of treatment appearing on said means for display, while gripping the instrument and operating said means for control with one hand, leaving the other hand free as he conducts therapy on a hemorrhoidal lesion.

2. The instrument of claim 1 wherein said means for display of status of treatment conditions of said instrument includes means for display of elapsed time of treatment.

3. The instrument of claim 1 wherein said means for display of status of treatment conditions of said instrument includes means for display of direct current intensity of treatment.

4. The instrument of claim 1 wherein said means for display of status of treatment conditions of said instrument includes means for display of actuation status of said treatment.

5. The instrument of claim 1 wherein said means for control comprises first means for increasing the level of current, and second means for decreasing the level of current.

6. The instrument of claim 5 wherein said means for control further comprises third means for ceasing direct current.

7. The instrument of claim 6 wherein said third means is actuated by simultaneous actuation of said first means and said second means.

8. The instrument of claim 1 wherein said obtuse angle is of the order of about 120°.

9. The instrument of claim 1 wherein said cooperative means comprises:
  said probe base comprising a key of predetermined size and shape, and said instrument handpiece defining a keyway adapted to receive said key therewithin in electricity-conducting coupled relationship.

10. The instrument of claim 9 wherein said key, taken in cross section, has the general form of a square with radiused corners of predetermined dimension corresponding to, but slightly less than, dimensions of said keyway.

11. The instrument of claim 1 or 9 wherein said probe comprises at least two elongated probe electrodes disposed in parallel array, and aid cooperative means for coupling said probe base to said handpiece is adapted for separation of a first said probe from said handpiece and engagement of a second said probe in coupled engagement with said handpiece.

12. The medical instrument of claim 11 wherein at least two distal tips of said elongated probe are longitudinally offset from each other.

13. An instrument for direct current electrical therapy of hemorrhoidal lesions or the like in a patient, employing a D.C. electric generator means, a grounding pad for the patient, a monopolar probe having a distal tip for penetration of the hemorrhoidal lesion to act as a negative electrode, and an instrument handpiece for support of the probe and control of the level of direct current, said probe comprising a base and, extending therefrom, at least one elongated probe electrode terminating in said distal tip adapted for electricity-conducting engagement with hemorrhoidal lesion, said instrument handpiece comprising:
a lower handle portion sized and constructed to be gripped by a physician,
cooperative means for coupling said probe base to said handpiece in electricity-conducting engagement, with the axis of said probe at an obtuse angle to the axis of said lower handle portion, arrangement of said probe and said lower handle portion at said obtuse angle allowing a physician to hold said instrument handpiece during treatment of a hemorrhoidal lesion without extended abnormal flexure of the wrist, said probe base comprising a key of predetermined size and shape, and said instrument handpiece defining a keyway adapted to receive said key therewithin in electricity-conducting coupled relationship, said key, taken in cross section, having the general form of a square with radiused corners of predetermined dimension corresponding to, but slightly less than, dimensions of said keyway,
a therapy-monitoring and control upper handle portion disposed generally above said lower handle portion and having a front panel visible to the physician when the probe distal tip is penetrated into a hemorrhoidal lesion, said front panel comprising
means for display of status of treatment conditions of said instrument, comprising means for display of elapsed time of treatment, means for display of direct current intensity of treatment and means for display of actuation status of said treatment, said means for display and the distal tip of said probe being disposed generally in the same line of sight of a physician holding said lower handle portion with said distal probe tip penetrated into a hemorrhoidal lesion, and
means for control of the level of direct current disposed adjacent said lower handle portion in a manner to allow a physician to operate said means for control with digits of a hand gripping said lower handle portion, said means for control comprising at least a first means for increasing the level of current, and second means for decreasing the level of current,
whereby a physician may simultaneously view a treatment site and observe conditions of treatment appearing on said means for display, while gripping the instrument and operating said means for control with one hand, leaving the other hand free as he conducts therapy on a hemorrhoidal lesion.

14. A probe adapted for use with an instrument for direct current electrical therapy of hemorrhoidal lesions or the like in a patient, employing a D.C. electric generator means, a grounding pad for the patient, and an instrument handpiece for support of the probe and control of the level of direct current, said probe comprising a base and, extending therefrom, at least one elongated monopolar probe electrode terminating in a distal tip adapted for electricity-conducting engagement with a hemorrhoidal lesion, and said probe further comprising cooperative means for coupling said probe base to the handpiece in electricity-conducting engagement, with the axis of said probe at an obtuse angle to the axis of the handpiece, arrangement of said probe and lower handle portion at said obtuse angle allowing a physician to hold said instrument during treatment of a hemorrhoidal lesion without extended abnormal flexure of the wrist, said probe base comprising a key of predetermined size and shape, and said instrument handpiece defining a keyway adapted to receive said key therewithin in electricity-conducting coupled relationship, said key, taken in cross section, having the general form of a square with radiused corners of predetermined dimension corresponding to, but slightly less than, dimensions of said keyway.

* * * * *